US00PP11730P2

(12) United States Plant Patent
Collicutt et al.

(10) Patent No.: US PP11,730 P2
(45) Date of Patent: Jan. 2, 2001

(54) SHRUB ROSE PLANT NAMED 'MORDEN SNOWBEAUTY'

(75) Inventors: Lynn M. Collicutt, Lowe Farm; Campbell G. Davidson, Morden, both of (CA)

(73) Assignee: Her Majesty the Queen in right of Canada, as represented by the Minister of Agriculture, Ottawa (CA)

( * ) Notice: Under 35 U.S.C. 154(b), the term of this patent shall be extended for 0 days.

(21) Appl. No.: 09/217,821

(22) Filed: Dec. 22, 1998

(51) Int. Cl.[7] ..... A01H 5/00
(52) U.S. Cl. ..... Plt./103
(58) Field of Search ..... Plt./102, 103

*Primary Examiner*—Howard J. Locker
(74) *Attorney, Agent, or Firm*—Burns, Doane, Swecker & Mathis, L.L.P.

(57) ABSTRACT

A new and distinct variety of shrub rose plant is provided which forms in clusters attractive semi-double somewhat flattened white blossoms. An open and semi-erect growth habit of excellent form is exhibited. The foliage is glossy dark green and contrasts nicely with the white blossoms. The plant propagates well by the use of softwood cuttings and possesses good winter hardiness. Petaloid stamens commonly are present. Excellent disease resistance particularly to blackspot its exhibited. It is particularly well suited for growing as an individual plant or as a mass planting to create ornamentation in the landscape.

3 Drawing Sheets

SUMMARY OF THE INVENTION

The new variety of shrub rose plant (*Rosa hybrida*) of the present invention was created through a complex pedigree controlled breeding program that was carried out at Morden, Manitoba, Canada. The 'Adelaide Hoodless' variety was crossed with *Rosa arkansana* Porter to obtain an offspring that was crossed with the 'Mount Shasta' variety. This cross produced a parent used in the creation of the new variety. The other parent of the new variety was formed by the crossing of the 'Prairie Princess' variety and the 'Morden Amorette' variety. None of the plants used to create the new variety have been patented in the United States. The 'Prairie Princess' variety is a shrub rose (Rosa sp.) developed by G. Buck in 1972 and the 'Mount Shasta' variety is grandiflora rose (Rosa sp.) developed by Swim and Weeks during 1963. The 'Morden Amorette' variety and the 'Adelaide Hoodless' variety are members of the PARKLAND Series of roses. *Rosa arkansana* Porter is a prairie hardy native tetraploid rose found in the Great Plains region of North America. The final cross of the breeding program was completed during 1984.

The parentage of the new variety can be summarized as follows:

['Prairie Princess'×'Morden Amorette']×['Mount Shasta'×('Adelaide Hoodless'×*Rosa arkansana* Porter)].

It was found that a single plant of the new variety of shrub rose plant of the present invention was created through the above-identified breeding program which possesses the following combination of characteristics:

(a) exhibits an open and semi-erect growth habit, (b) forms clusters of attractive semi-double somewhat flattened white blossoms, (c) forms attractive glossy dark green foliage, (b) propagates well by the use of softwood cuttings, (e) exhibits good winter hardiness, (f) exhibits excellent disease resistance, and (g) is particularly well suited for growing as ornamentation in the landscape.

Rose plants of the new variety can be grown well on their own roots outdoors without protection at Morden, Manitoba, Canada. Blossom production commonly begins in early June at Morden, Manitoba, Canada and commonly is completed by mid-September. Good blossom coverage (e.g., up to approximately 30 percent or more of the entire plant at week three of blooming) is achieved which contrasts nicely with the attractive dark green foliage.

Accordingly, the new variety well meets the needs of the horticultural industry. It can be grown to advantage as attractive ornamentation as an individual plant or as a mass planting in parks, gardens, public areas, and residential landscapes.

The characteristics of the new variety have been found to be homogenous and stable and have been shown to be strictly transmissible by asexual propagation by the rooting of softwood stem cuttings conducted at Morden, Manitoba, Canada.

The new variety initially was designated 84J3T403 and X6 and subsequently has been named the 'Morden Snowbeauty', The name was selected to reflect the white flower coloration and the excellent field performance of the plant. It constitutes an attractive white-flowered member of the PARKLAND Series of roses.

BRIEF DESCRIPTION OF THE PHOTOGRAPHS

The accompanying photographs show as nearly true as is reasonably possible typical specimens of the plant, blossoms, and foliage of the new variety. The plants were photographed during the summer while growing in the landscape on their own roots at Morden, Manitoba, Canada. The plant age was approximately five years including the year required to root the cutting.

DETAILED DESCRIPTION

Figure 1:
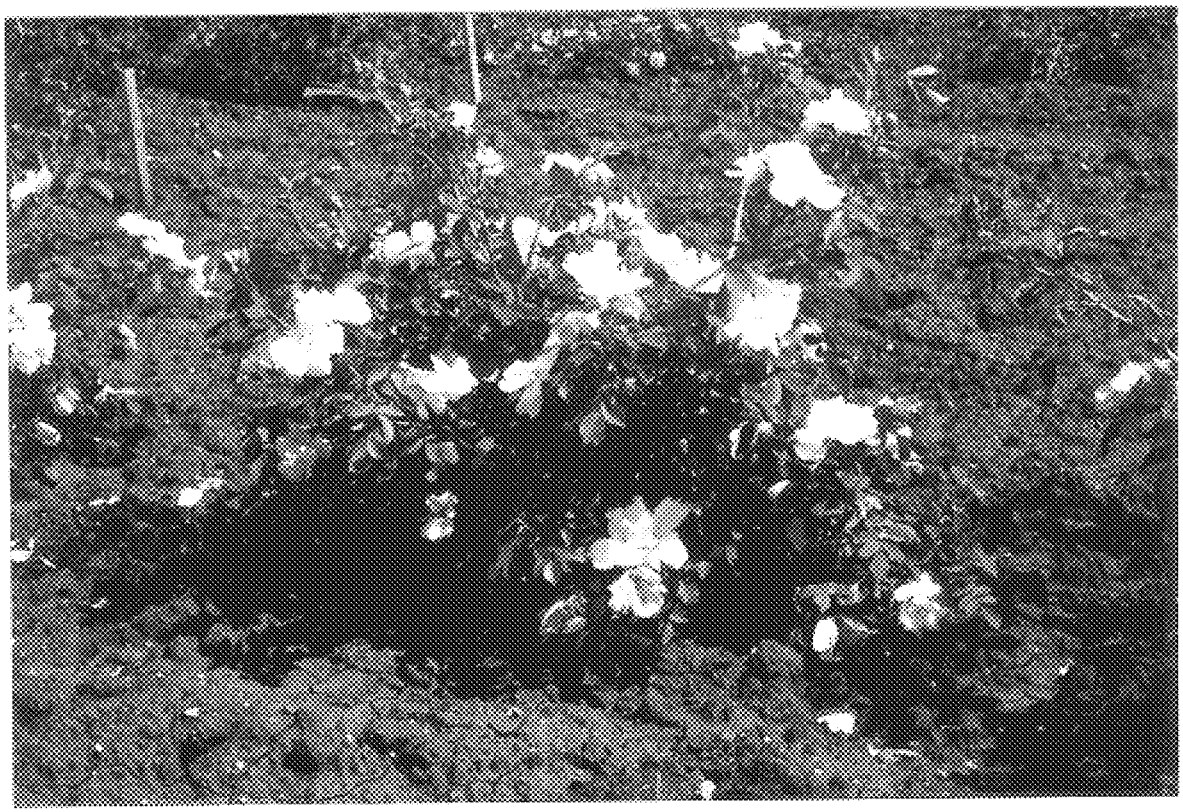
FIG. 1 illustrates a typical mature plant of the new variety. The semi-erect upright growth habit is shown.
Figure 2:
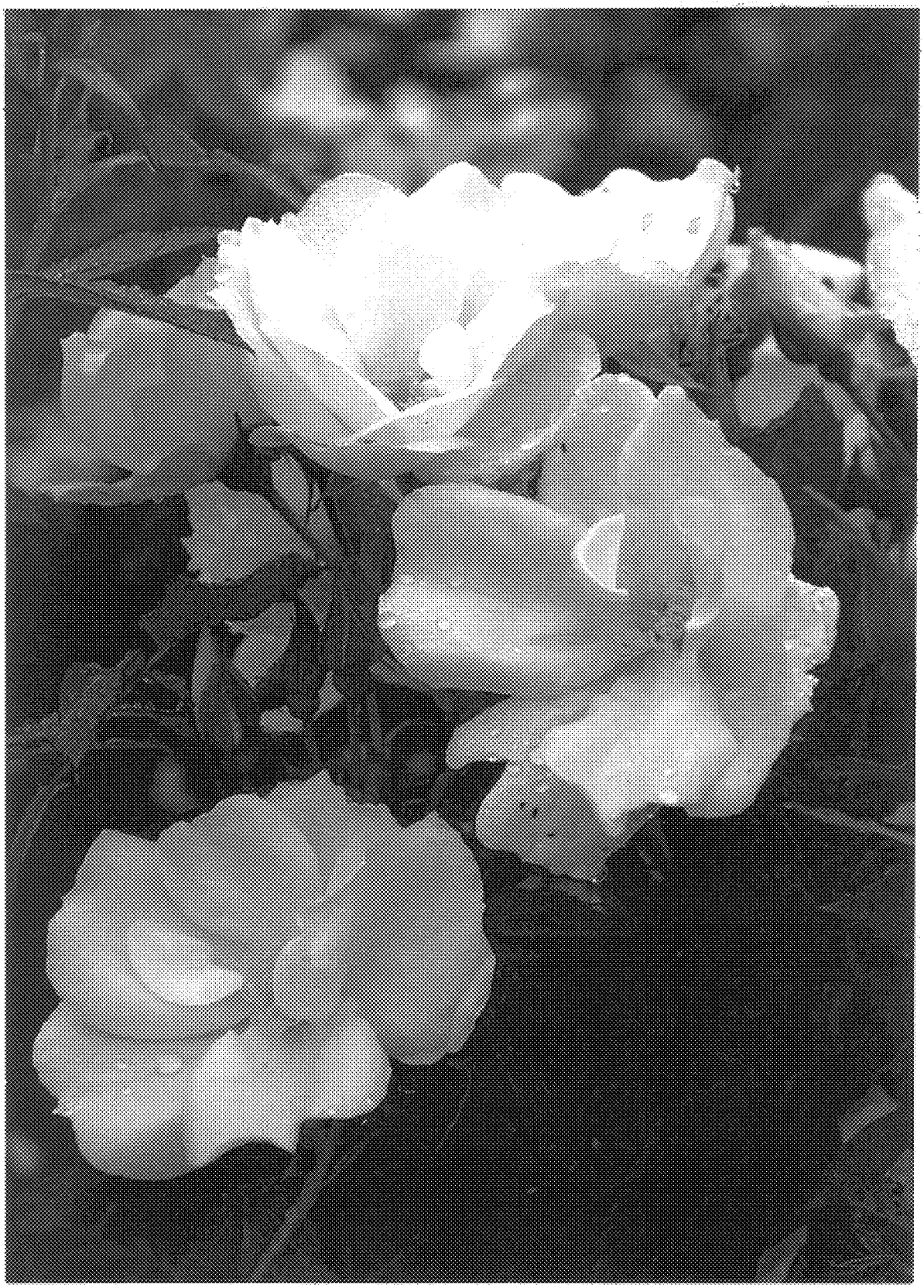
FIG. 2 illustrates a cluster of typical white semi-double almost flat blossoms, as well as an unopened bud.
Figure 3:
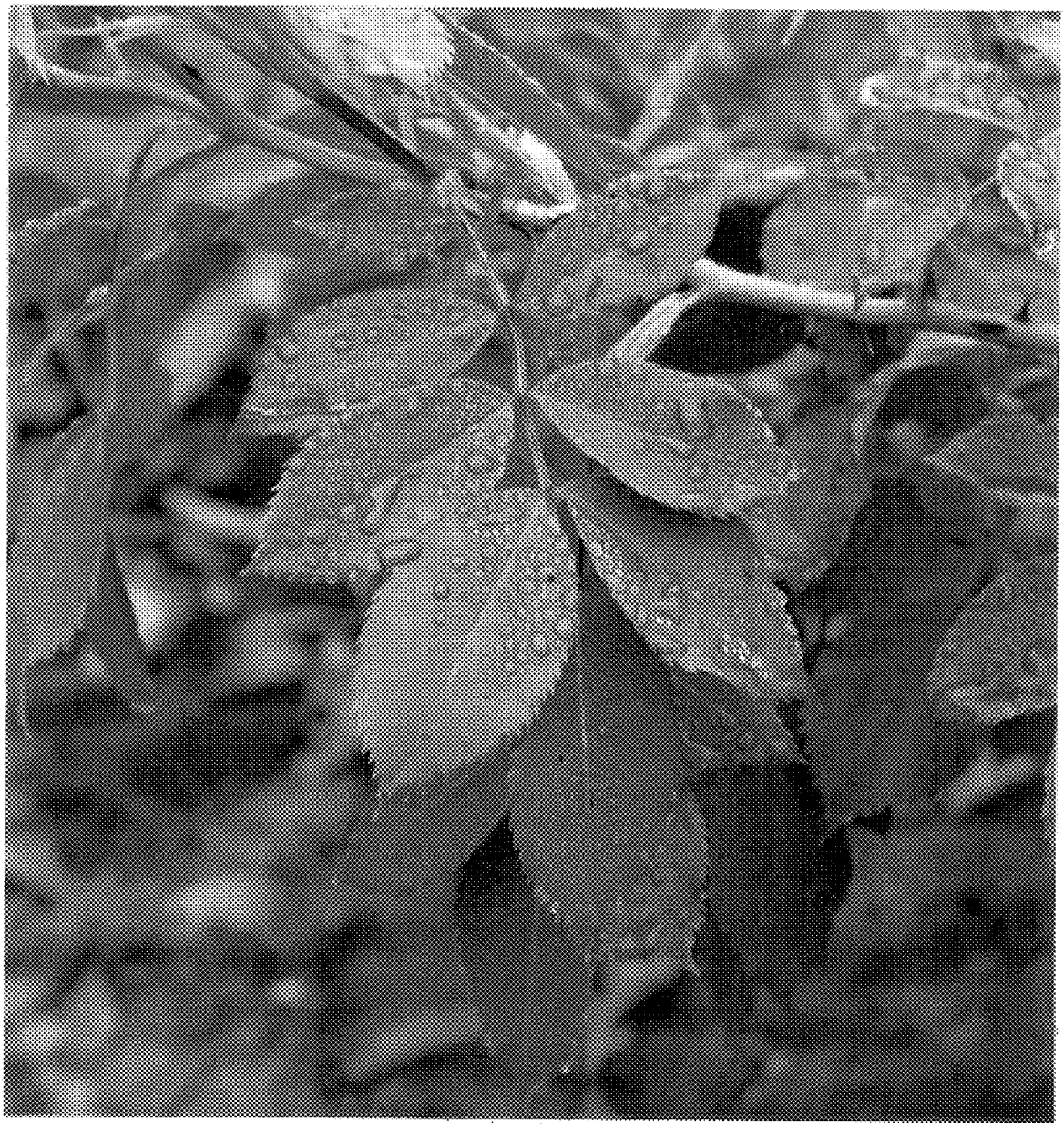
FIG. 3 illustrates typical foliage.

The chart used in the identification of colors is that of The Royal Horticultural Society (R.H.S. Colour Chart). Common color terms are to be accorded their ordinary dictionary significance. The description is based on the observation of mature plants while growing on their own roots outdoors in the landscape during the summer at Morden, Manitoba, Canada.

Class: Shrub.

Plant:

*Height.*—Approximately 31 to 96 cm. with a mean height of approximately 74 cm. Juvenile cane growth is more arching and less erect than subsequent growth. A fully mature plant commonly can assume a height of approximately 85 cm. The plant height and plant width vary considerably with environmental conditions. Greater dimensions are produced with warmer temperatures, greater precipitation, and with fertilization (primarily nitrogen).

*Width.*—Commonly approximately 46 to 128 cm. with a mean width of approximately 98 cm.

*Habit.*—Semi-erect, upright, and spreading.

Bark: Current season bark is Yellow-Green Group 144B and gradually changes to Yellow-Green Group 144A on mature stems.

Thorns: Mature stems typically bear a sparse to moderate quantity of reflexed prickles commonly having a length of approximately 3 to 7 mm. and an average length of approximately 5 mm. On the current season growth smaller prickles commonly also are present. The coloration is Greyed-Purple Group 187B on young stems and Greyed-Purple Group 187A on mature stems older than one year.

Leaves: Compound and pinnate.

*Leaflets.*—Number: Commonly 3 to 9 with 7 leaflets being the most common. Configuration: Acute with a smoothly rounded base. Margins: Serrate. Size: Terminal leaflets commonly rante from approximately 2.1 to 7.5 cm. in length (mean approximately 5.9 cm.) and approximately 2.4 to 4.8 cm. in width (mean approximately 3.8 cm). General appearance: Dark green, and glossy. Petiolules: Very small and commonly <2 mm.

*Color.*—Adult foliage: Shiny dark green, Green Group 137A on the upper surface and lighter dull green, Green Group 138B the under surface. Young stems: Yellow-Green Group 144A with a slightly reddish margin of Greyed-Red Group 178A. Petioles: Green Group 137B, and possess a distinct groove.

Inflorescence:

*Number of flowers.*—Commonly in clusters of 3 to 10, and in clusters of 5 on average. Peak flower cover has been observed in mid- to late-June.

*Sepals.*—Commonly 2 to 3 cm. in length, Green Group 143C on the outer surface and Yellow-Green Group 148D on the inner surface with a tomentose inner surface.

*Buds.*—Shape: Acutely pointed. Color upon opening: Green-White Group 157A.

*Flower.*—Shape: Tends to flatten when fully open as shown in the photograph. The depth of the somewhat flattened flowers tends to be approximately 2 cm. when fully open. Diameter: Commonly approximately 6 to 12 cm., and 8 cm. on average. Color (when blooming): When fully open white as illustrated, White Group 155A on both surfaces. When only partially open slight pink tones sometimes are included in cooler weather. When fully mature, a slight petal edging of brown may be present. The base of the petals on the underside sometimes is pale yellow, near Yellow group 2C. Fragrance: Weak. Petal number: Commonly approximately 7 to 18. Petal configuration: Smooth and orbicular with rounded tips with reflexed outer edges. In many instances the midribs commonly are raised. Petal size: Commonly approximately 2.2. to 3.3 cm. in length (mean 2.8 cm.) and approximately 1.8 to 3.6 cm. in width (mean 2.6 cm.). Stamens: Several petaloid stamens commonly are present having a width of approximately 1 to 2 cm., the anthers produce fertile pollen and are medium yellow in coloration. Filaments: Commonly are nearly completely white. Peduncle: Commonly approximately 28 mm in length on average, moderate in strength, under heavy flower production may bend causing a slightly drooping appearance, the coloration is Yellow-Green Group 144B, and a few small prickles sometimes are present. Pedicel: Similar in appearance to the peduncle, and commonly approximately ¾ the size of the peduncle. Style: Yellow and of medium length. The stigmas commonly are exserted slightly. Receptacle: Round, Green Group 138B in coloration, and generally less than 2 cm. in diameter. Hips: Are formed each season but commonly do not ripen fully under the specified growing conditions. Lasting quality: Long lasting approximately 7 to 14 days on the plant and approximately 7 to 10 days when cut and placed in a vase. Warmer and drier conditions tend to shorten the bloom life on the plant. Petal drop: The petals detach well upon maturity with strong winds tending to remove the older petals quickly.

Development:

*Vegetation.*—Good vigor.

*Blossoming.*—Commonly begins in early June on previous season buds and continues on current season growth until approximately the middle of September. The mean flower duration is 14 weeks. The percent coverage of the blossoms compares favorably to that of other roses of PARKLAND Series and other white-flowered shrub roses under the specified growing conditions.

*Hardiness.*—Has survived in Agriculture Canada Hardiness Zone No. 2 with no protection. See Quellet and Sherk, *Can. J. Plant Sci.*, 47:3513–3518 (1967). Some stem dieback may occur in severe winters, but regrowth is very good.

*Resistance to diseases.*—Resistance is excellent to local populations of blackspot (*Diplocarpon rosae* Wolf.), powdery mildew [*Sphaerotheca pannosa* (Wallr, ex Fr.) Lev.], and rust (Phragmidium sp.).

*Preferred mode of propagation.*—The use of softwood cuttings to produce self-rooted plants is recommended. For instance, softwood cuttings of 1 to 3 nodes in length can be taken during late spring through mid-summer, treated with rooting hormone (e.g., 3000 to 5000 ppm indole-butyric acid) and placed under intermittent mist or fog to achieve high rates of propagation which commonly exceed 85 percent. Tissue culture also can be used for propagation. Budded or grafted roses may suffer winter injury at the specified growing location.

We claim:

1. A new and distinct variety of shrub rose plant characterized by the following combination of characteristics:

(a) exhibits an open and semi-erect growth habit, (b) forms in clusters attractive semi-double somewhat flattened white blossoms, (c) forms attractive glossy dark green foliage, (d) propagates well by the use of softwood cuttings, (e) exhibits good winter hardiness, (f) exhibits excellent disease resistance, and (g) is particularly well suited for growing as ornamentation in the landscape;

substantially as herein shown and described.

* * * * *